(12) United States Patent
Roizman

(10) Patent No.: US 10,101,313 B2
(45) Date of Patent: Oct. 16, 2018

(54) METHOD AND APPARATUS FOR CONTINUOUS MONITORING OF QUALITY AND MOISTURE PARAMETERS OF LIQUIDS

(71) Applicant: IntellPower Pty Ltd., Carnegie, Victoria (AU)

(72) Inventor: Oleg Roizman, Helsinki (FI)

(73) Assignee: IntellPower Pty Ltd., Carnegie, Victoria (AU)

( * ) Notice: Subject to any disclaimer, the term of this patent is extended or adjusted under 35 U.S.C. 154(b) by 151 days.

(21) Appl. No.: 15/035,030

(22) PCT Filed: May 13, 2014

(86) PCT No.: PCT/FI2014/050359
§ 371 (c)(1),
(2) Date: May 6, 2016

(87) PCT Pub. No.: WO2015/067844
PCT Pub. Date: May 14, 2015

(65) Prior Publication Data
US 2016/0290985 A1 Oct. 6, 2016

(30) Foreign Application Priority Data

Nov. 6, 2013 (AU) ............................... 2013904288
Dec. 18, 2013 (FI) ..................................... 20136281

(51) Int. Cl.
*G01N 25/58* (2006.01)
*G01N 33/28* (2006.01)

(52) U.S. Cl.
CPC ......... *G01N 33/2847* (2013.01); *G01N 25/58* (2013.01)

(58) Field of Classification Search
CPC ........................... G01N 25/58; G01N 33/2847
See application file for complete search history.

(56) References Cited

U.S. PATENT DOCUMENTS 6,809,528 B1 10/2004 Stormbom et al.
7,036,356 B2 5/2006 Leppaenen et al.
(Continued)

FOREIGN PATENT DOCUMENTS

CN 2486972 4/2002
CN 101067617 11/2007
(Continued)

OTHER PUBLICATIONS

Gradnik et al., "Experimental Evaluation of Water Content Determination in Transformer Oil by Moisture Sensor," in Proceedings of the 2011 IEEE International Conference on Dielectric Liquids (ICDL), pp. 1-4, 2011.
(Continued)

*Primary Examiner* — Bryan Bui
(74) *Attorney, Agent, or Firm* — Sand & Sebolt

(57) ABSTRACT

This application relates to a method and a system for determining aging of a liquid. The method includes steps for measuring a relative water content ($rS_1$) of the liquid in a first measurement step at a first temperature ($T_1$), measuring the relative water content ($rS_2$) at a second temperature ($T_2$) in a second measurement step, the first and second measurement step are performed such that absolute water content (w) stays essentially unchanged between these two measurements, and based on these at least two measurement values ($rS_1$, $T_1$, $rS_2$, $T_2$), determining a first water in oil solubility coefficient (B) for the liquid. In accordance with the invention the first water in oil solubility coefficient (B) is monitored essentially continuously in order to determine the liquid quality.

8 Claims, 3 Drawing Sheets

(56) References Cited

U.S. PATENT DOCUMENTS

| | | | | |
|---|---|---|---|---|
| 2004/0154384 A1* | 8/2004 | Leppanen | ............... | G01N 25/56 |
| | | | | 73/61.46 |
| 2008/0218666 A1* | 9/2008 | Toyooka | ........... | G02F 1/133528 |
| | | | | 349/96 |
| 2011/0246088 A1* | 10/2011 | Santos | ................ | G01N 33/2841 |
| | | | | 702/24 |

FOREIGN PATENT DOCUMENTS

| | | |
|---|---|---|
| CN | 101713721 | 5/2010 |
| CN | 102081064 | 6/2011 |
| CN | 102411045 | 4/2012 |
| ES | 2253979 | 1/2006 |
| WO | 02/093147 | 11/2002 |
| WO | 2007/038845 | 4/2007 |

OTHER PUBLICATIONS

Du et al., "Mousture Solubility for Differently Conditioned Transformer Oils," in IEEE Transactions on Dielectrics and Electrical Insulation, vol. 8 No. 5, pp. 805-811, 2001.

Gan et al., "Analysis of Water Solubility in Transformer Oil Using Least Square Fitting Method," in 2010 International Conference on High Voltage Engineering and Application (ICHVE), pp. 93-95, 2010.

Oommen, "On-Line Moisture Sensing in Transformers," in Proceedings of the 20th Electrical Electronics Insulation Conference, pp. 236-240, 1991.

Shkolnik, "Determination of Water Content in transformer Insulation," in Proceedings of the 2002 IEEE International conference in Dielectric Liquids (ICDL), pp. 337-350, 2002.

\* cited by examiner

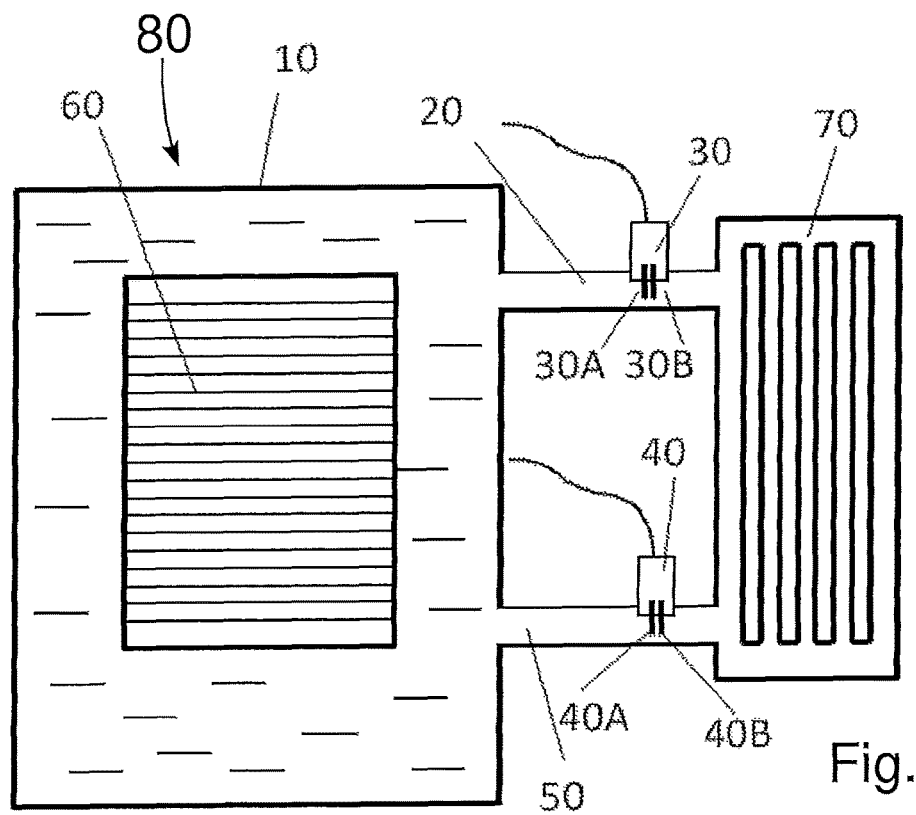
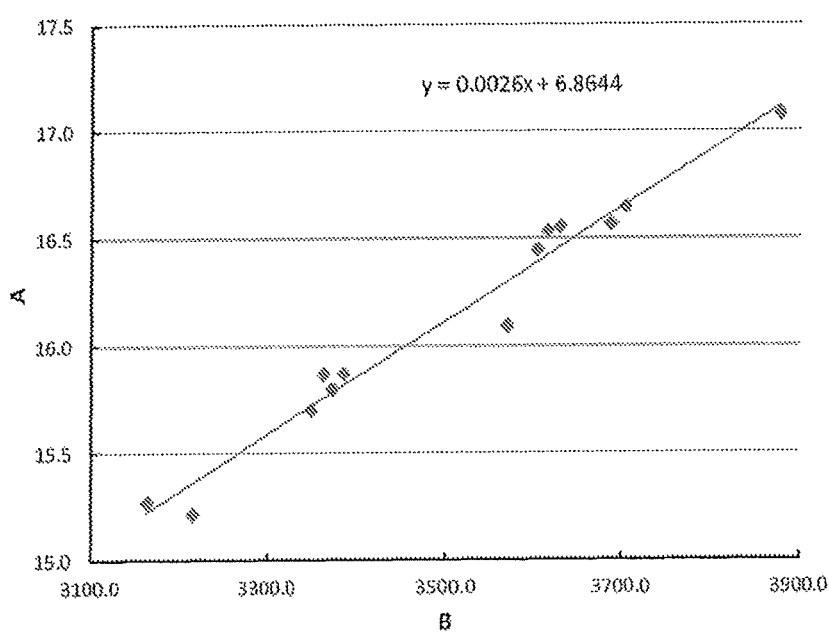
Fig. 1
Fig. 2A

METHOD AND APPARATUS FOR CONTINUOUS MONITORING OF QUALITY AND MOISTURE PARAMETERS OF LIQUIDS

BACKGROUND OF THE INVENTION

Technical Field

The present invention relates to the field of condition monitoring and diagnostics liquids, in preferred embodiments of the invention liquids of power electrical equipment and is more particularly concerned with a method and means for online monitoring of insulating liquid quality and parameters related to presence of water in a liquid dielectric.

Background Information

A presence of water (also known as moisture) in insulating liquid is one of the greatest concerns for reliable operation of electrical equipment including large, medium and small liquid filled transformers. The water is harmful for both liquid and solid insulation; it accelerates aging and severely compromises dielectric integrity of any electrical apparatus. Therefore an assessment of water content in both liquid and solid insulation is critical and essential part of any condition based monitoring programs.

When a power transformer is manufactured its insulation system has low water content. As the transformer ages, water is transferred into the insulation either by ingress from outside the transformer or by chemical decomposition of the insulation materials. The solubility of water in insulating material changes considerably as the insulating liquid ages. The water parameters, including absolute and relative water content in the insulation along with its solubility characteristics, may therefore be used to indicate the condition of the insulating liquid and health of the transformer as a whole.

Traditionally, for determination of water content in the insulating liquid chemical methods, such as Karl Fischer titration, have been used. These methods are labor intensive, use dangerous reagents and can only be used in the laboratory, thus are not suitable for continuous online assessment. Another drawback of the laboratory methods is a possibility for error as a result of measurement uncertainty, cumbersome sampling procedures and human errors.

During the last decade online moisture sensors, based on capacitive polymer thin film technology, have been successfully used for determination of relative saturation of water in oil measured in percentage. These sensors generally do not provide for the determination of absolute water content measured, for example, in mg/kg, and therefore can't be utilized for benchmarking, trending and moisture assessment conforming to relevant industry standards and guidelines.

U.S. Pat. No. 6,809,528 describes a method and apparatus for measuring the water content of a liquid, where the properties of the liquid are measured using both relative-value and absolute-value measurement method. To accomplish this task two different methods are used simultaneously, one is directly measuring relative to saturation value of water content of a liquid and another is a prediction of absolute value of water content by measuring the liquid dielectric constant.

It is well known that dielectric constant is dependent on type, chemical composition, acidity and moisture content of insulating liquid. The invention describes a method to calculate dielectric constant of dry liquid and therefore absolute water content is possible to calculate but as the water content of insulation liquids are low a needed performance of the dielectric constant measurement is difficult to achieve. For those reasons an implementation of the described invention is very limited.

U.S. Pat. No. 7,036,356 describes a method and apparatus for measurement of total water content in a liquid. According to the method, the relative water content (aw) of the liquid is measured in a first measurement step at a first temperature (T1). According to the publication, the temperature of the liquid under measurement is altered from the first temperature (T1) and the relative water content is measured in a second measurement step at the second, altered temperature (T2), whereby, based on these at least two measurement values (aw(1)T 10 aw(2)T 2), the total water content is determined from the temperature dependence of water dissolution into the liquid under measurement.

U.S. Pat. No. 5,644,239 describes a method where measurements of dielectric characteristics of liquid are used for calculating a quality parameter of the liquid. The method includes a means for measuring opacity of the said liquid along with the means of measuring liquid conductivity. It is known that conductivity of a liquid is dependent on water content, chemical composition, acidity and other contaminants. It is difficult if not impossible to distinguish effects of various parameters on oil quality and degree to which extend liquid is affected by any particular parameter.

Because of their relatively high cost and complexity, none of these methods and devices has achieved any substantial degree of commercial success and there accordingly exists a need for a reliable low cost, simple, method and apparatus for measuring the quality of insulating liquid along with absolute water content and water solubility characteristics of the insulating liquid.

It is, therefore, an objective of the present invention to provide a practical method and apparatus for identifying the absolute water content of insulating liquid, water solubility coefficients, including Henry's law constant for the said insulating liquid.

Another objective of the invention is to provide a measure for identifying the condition of insulating liquid, such as liquid quality index.

SUMMARY

The present invention is based on the objective for determining aging of a liquid by temperature and humidity measurements.

These and other objects are achieved by the present invention, as hereinafter described and claimed. Thus the invention concerns which method comprises steps for measuring a relative water content ($rS_1$) of the liquid in a first measurement step at a first temperature ($T_1$), measuring the relative water content ($rS_2$) at a second temperature ($T_2$) in a second measurement step, the first and second measurement step are performed such that absolute water content (w) stays essentially unchanged between these two measurements, determining a first water in oil solubility coefficient (B) for the liquid such that the first water in oil solubility coefficient (B) is monitored essentially continuously in order to determine the liquid quality.

A method preferably includes that the first water in oil solubility coefficient (B) is defined as a function of said $rS_1$, $T_1$, $rS_2$ and $T_2$.

A method preferably includes that the first water in oil solubility coefficient is defined as, $$B = \frac{\ln\left(\frac{rS_1}{rS_2}\right)}{\left(\frac{1}{T_2} - \frac{1}{T_1}\right)}$$

or other mathematical solution.

A method preferably includes that a liquid quality index (LQI) is formed as a function of B.

A method preferably includes that a liquid quality index (LQI) is formed based on equation, $$LQI = 1 - \frac{B_{max} - B}{B_{max} - B_{min}},$$

or other mathematical solution.

A method preferably includes that determining a second oil solubility coefficient (A) by forming mathematical relationship between the first (B) and second oil solubility coefficient (A) for an oil type by laboratory measurements (FIG. 2), using this mathematical relationship for solving the second oil solubility coefficient (A) from the first oil solubility coefficient (B) and determining absolute water content from equation, $$w = \frac{rS \times \exp\left(A - \frac{B}{T}\right)}{100}$$

or other mathematical solution.

A method preferably includes that regression method is used as a mathematical relationship.

A method preferably includes that the oil of a transformer is evaluated.

A method preferably includes that the measurements are performed with two humidity sensors including temperature sensors located in positions of the measurement object such that during measurement there is temperature difference between the sensors.

A method preferably includes that the measurements are performed with one humidity sensor including temperature sensors with a by-pass pipe and valves for feeding the liquid to the by-pass pipe for alternating the temperature of the liquid to be measured.

A method preferably includes locating the sensors in different heights relative to each other.

A method preferably includes locating the sensors in in- and outlet of a cooler for the liquid.

A method preferably includes locating the sensors in in- or outlet of a oil dryer.

It is a novel approach to measure the insulating liquid quality by observing a change in water solubility characteristics of a liquid.

BENEFITS OF THE INVENTION

With help of the invention liquid quality of various objects may be monitored on-line. This is cost saving especially with large units like transformers, where aged liquid may cause serious damage to the transformer.

With on line measurement cost are saved also compared to methods where the liquid is tested in laboratory based on samples collected on site from the transformer.

BRIEF DESCRIPTION OF THE SEVERAL VIEWS OF THE DRAWINGS

FIG. 1 is a schematic view of a transformer equipped with moisture and temperature sensors which constitute the apparatus of the present invention.

FIG. 2A is the graphical representation of a relationship between solubility coefficients A and B.

DETAILED DESCRIPTION

Figure 2B:
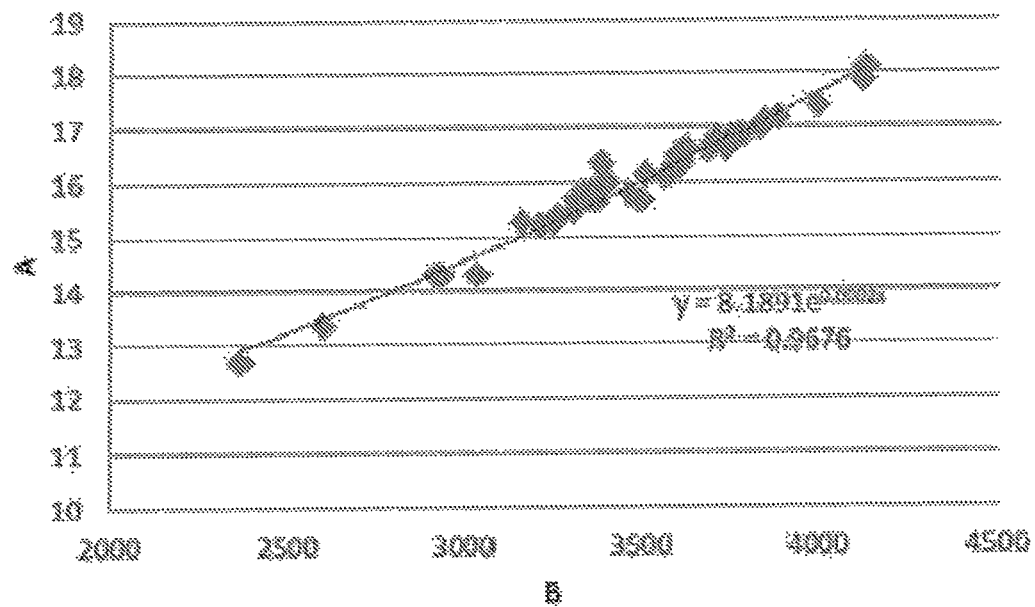
FIG. 2B is another graphical representation of a relationship between solubility coefficients A and B.

For purposes of illustration only and not to limit generality, the present invention will now be explained with reference to the model of an oil filled large power transformer. However, it should be recognized that the present invention is applicable to other types of liquid-filled electrical equipment, such as instrument transformers, autotransformers, rectifier transformers, reactors and tap changers.

For one skilled in the art it should not be difficult to see that the present invention could also be utilized in a laboratory environment where testing of dielectric liquid for moisture content and the liquid quality. When used in the laboratory environment it should also be recognized that the current invention can be used for non-insulating liquids such as lubricating and hydraulic oils.

FIG. 1 illustrates an example of a power transformer comprising a tank 10, top cooler pipe 20; top moisture and temperature probe 30 with embedded top temperature sensor 30A and top moisture sensor 30B; bottom moisture probe 40 with embedded bottom temperature sensor 40A and bottom moisture sensor 40B; and a bottom cooler pipe 50. All said sensors are commercially available.

The insulating liquid is heated by electrical losses caused by alternating current flowing through the windings 60 in a way that the liquid is usually hotter at the top and it is cooler at the bottom of a transformer tank 10. In such an arrangement the insulating liquid serves as a coolant as well as an insulator. The liquid is cooled by the cooling device 70, which could be one of various designs, such as a radiator based on natural heat convection or assisted by a fan, or a water cooler assisted by a pump.

The moisture sensors 30B and 40B measure relative saturation of water in the liquid at above locations.

To determine the absolute water content of the liquid the following formula is well known in the art:

$$w = rS \times \exp\left(-A - \frac{B}{T}\right) / 100, \quad (1)$$

where w is the absolute water content (also known as water concentration) of the liquid, expressed in mg kg; rS— relative water saturation in %, which could be measured by one of the said relative saturation sensor, T is a thermodynamic temperature in Kelvin measured by the temperature sensor at the same location as said relative saturation; and A and B are the specific water solubility coefficients. Unfortunately, these A and B coefficients change as the liquid ages, which create difficulty in continuous determination of absolute water content w.

The function of water content at saturation versus temperature is known as water solubility curve, which represents important information about composition of the insulating liquid and its quality. The solubility coefficients are not independent and a relationship between the two is normally observed as depicted in FIG. 2.

It is well known in the art that by measuring temperature at two locations and relative water saturation at one of these locations (for example, bottom tank) the second (top) relative saturation value can be determined as:

$$rS_{to} = rS_{bo} \times \exp\left(B \times \left(\frac{1}{T_{bo}} - \frac{1}{T_{to}}\right)\right), \quad (2)$$

where $rS_{to}$ is the relative saturation of water in liquid at the top cooler pipe location; $rS_{bo}$ is the relative saturation of water in liquid at the bottom cooler pipe location; $T_{to}$ is the thermodynamic temperature at the top cooler pipe location and $T_{bo}$ is the thermodynamic temperature at the bottom cooler pipe location. In case where water content of the liquid remains constant during temperature change from $T_1$ to $T_2$ equation (2) is also valid for a single location. In this case relative saturation at the second temperature $rS_2$ can be determined from the relative saturation at the first temperature $rS_1$. Then equation (2) can be rewritten as:

$$rS_2 = rS_1 \times \exp\left(B \times \left(\frac{1}{T_2} - \frac{1}{T_2}\right)\right), \quad (2a)$$

This is a core idea of the present invention to measure and monitor the water solubility coefficients for determination of absolute moisture content and quality of insulating liquid.

It is well recognized in the art that during a transformer operation the solubility of water changes as the liquid ages. Therefore by monitoring the change in water solubility it is possible to relate that change to a change in liquid quality.

According to the invention the determination of moisture parameters is conducted as follows:

Firstly, provided that there is a substantial temperature gradient between top and bottom locations of the sensors 30A and 40A, the water in oil solubility coefficient B could be determined from (2) as:

$$B = \frac{\ln\left(\frac{rS_1}{rS_2}\right)}{\left(\frac{1}{T_2} - \frac{2}{T_1}\right)} \quad (3)$$

The substantial temperature gradient is e.g. more than 5° C. Of course, the water in oil solubility coefficient B could also be determined mathematically in several other ways and this formula is only an example of one embodiment of the invention. In other words the first water in oil solubility coefficient is defined as a function of said rS1, T1, rS2 and T2.

Then the Liquid Quality Index (LQI) could be calculated as a function of B, e.g:

$$LQI = 1 - \frac{B_{max} - B}{B_{max} - B_{min}}, \quad (4)$$

where $B_{max}$ and $B_{min}$ are the highest and lowest values of the solubility coefficient B, which varies from $B_{max}$, representing a new clean insulating liquid, to $B_{min}$, representing very aged (end of life) liquid. For example, for transformer mineral oil these values are known to be 3900 and 3100 respectively. In accordance with the invention also LQI could be defined in other mathematical presentations, e.g., as a function of B According to the current embodiment the LQI varies between 0 and 1.1 (one) is assigned to a new clean, not contaminated liquid and 0 (zero) is assigned to severely aged liquid, which needs to be replaced or reclaimed. Any other value of B coefficient is attributed to intermediate state of the liquid quality.

For determination of absolute water content of the said insulation liquid the calculation of solubility coefficient A is conducted following one of the methods:

(a) on-line, applying a linear relationship between A and B:

$$A = \alpha B + \beta, \quad (5)$$

where $\alpha$ and $\beta$ are unique for a certain type of insulating liquid. For example, for mineral oil these could be obtained by performing a linear regression as shown in FIG. 2A. In other words the dots in FIG. 2 are laboratory measurements for values A and B and $\alpha$ and $\beta$ are solved from this information by linear regression. In accordance with the invention also other, more complicated mathematical regressions could be used in order to determine the relation between A and B. e.g. as shown in FIG. 2B.

$$A = \alpha e^{\beta B}$$

(b) off-line, using Karl Fisher (KF) titration method according to the equation $$A = \ln\left(\frac{w}{rS} \times 100\right) + \frac{B}{T}, \quad (6)$$

where w is water concentration of the liquid sample obtained by KF titration.

(c) off-line, adding known amount of water to the liquid sample. This method does not require KF titration and has an obvious advantage of not using the re agents/consumables.

$$A = \ln\left(\frac{\Delta w}{\Delta rS} \times 100\right) + \frac{B}{T}, \quad (7)$$

where $\Delta w$ and $\Delta rS$ are the known amount of water in mg/kg of liquid added to the solution and the change in relative saturation respectively.

Once the solubility coefficients A and B are determined the absolute water content of the liquid at any of the said locations could be calculated by applying the formula (1) as:

$$w = \frac{rS \times \exp\left(A - \frac{B}{T}\right)}{100} \quad (8)$$

where rS and T are measured at the same location.

The Henry's law constant $k_H$ then for the said locations can be calculated by applying the formula:

$$k_H = \frac{\exp\left(A - \frac{B}{T}\right)}{p_s} \quad (9)$$

The following World Meteorological Organization (WMO, 2008) formulation for the saturated vapor pressure could be used in (9):

$$p_s = 6.112 \times \exp(17.62t/(243.12+t)),$$

where t is the temperature in Celsius, corresponding to thermodynamic temperature in (9).

Figure 3:
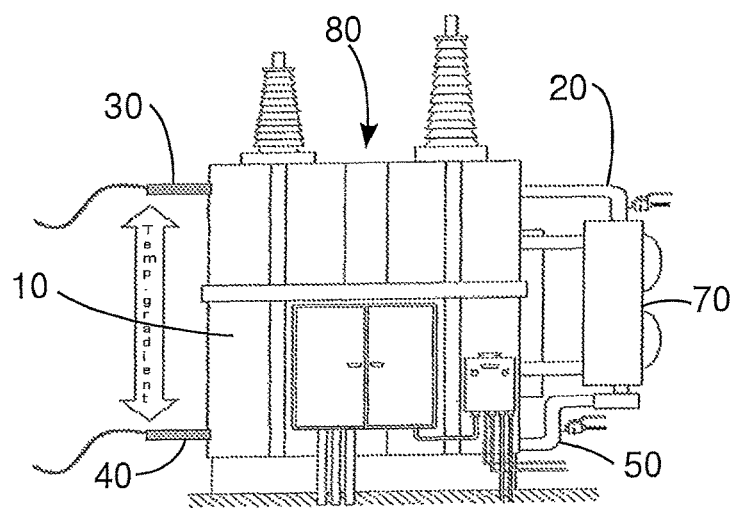
FIG. 3 is a schematic view of a transformer equipped with moisture and temperature sensors in accordance with another embodiment of the invention.

In accordance with FIG. 3 the probes 30 and 40 may be positioned directly to the top and bottom parts of the transformer 80 tank 10, because there is a temperature difference between the top and the bottom of the tank 10.

Figure 4:
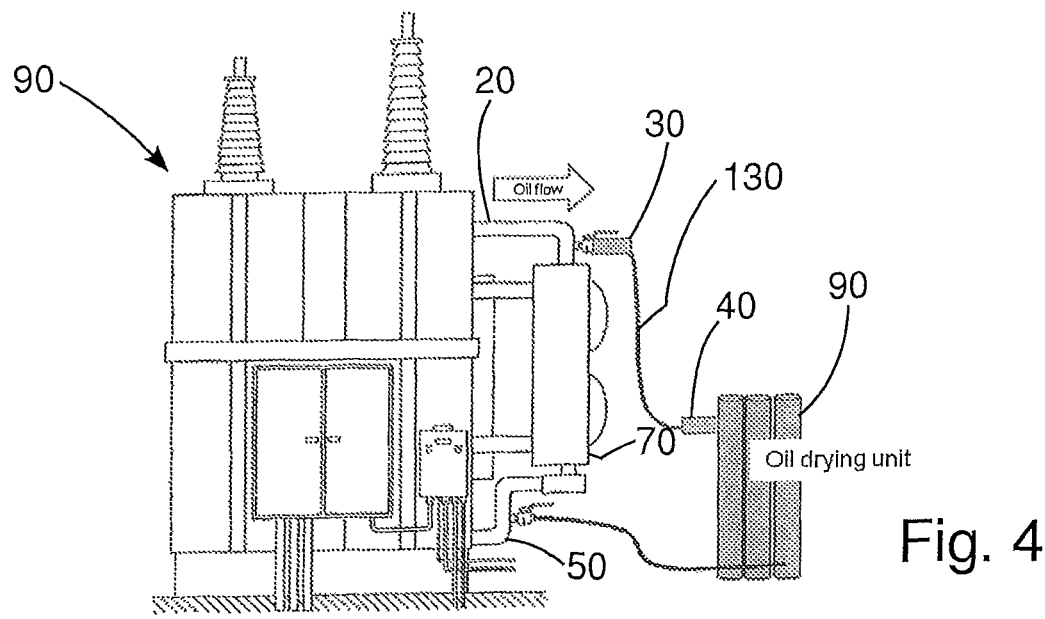
FIG. 4 is a schematic view of a transformer equipped with moisture and temperature sensors in accordance with another embodiment of the invention.

Alternatively in accordance with FIG. 4 the probes 30 an 40 may be positioned at the opposite ends of the input pipe 130 leading to oil drying unit 90.

Figure 5:
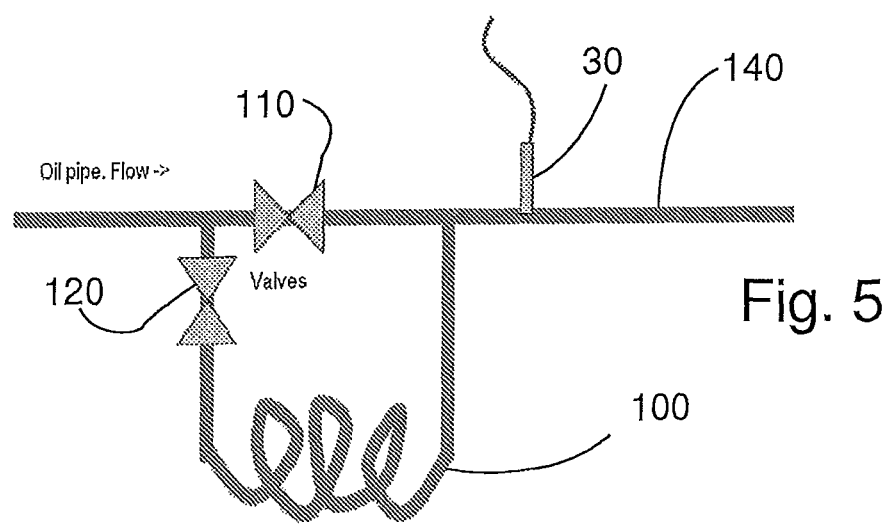
FIG. 5 is a schematic view of an alternative embodiment in accordance with the invention.

Alternatively in accordance with FIG. 5 the liquid to be analyzed may be fed to a measurement pipe 140 (like pipes 20, 50 or 130 in FIGS. 1 and 4) provided by a bypass pipe 100 and two valves 110 and 120 for feeding the liquid alternatively to the by-pass pipe 100 or directly to the pipe 140. The by-pass pipe 100 has either cooling or heating function for the liquid, hence the parameters of equations 2 and 2a may be obtained by one probe 30 only by a) closing valve 120 and opening valve 110 for obtaining parameters at first temperature, and b) closing valve 110 and opening valve 120 for obtaining parameters at second temperature.

The advantages of the present invention include, without limitation, that it is a method for determination of absolute water content of the insulating liquid and its water solubility characteristics, including Henry's law constant. Further, the method allows determination of liquid quality with the assistance of newly introduced liquid quality index.

While the foregoing written description of the invention enables one skilled in the art to make and use what is considered presently to be the best mode thereof, those skilled in the art will understand and appreciate the existence of variations, combinations, and equivalents of the specific embodiment, method, and examples herein. The invention should therefore not be limited by the above described embodiment, method, and examples, but by all embodiments and methods within the scope and spirit of the present invention.

Essentially continuous measurement means in this application e.g. regular measurements within predetermined intervals like minutes, hours or days. This could mean also e.g. 100-1000 measurements with predetermined intervals for the liquid to be evaluated during its lifetime.

Mathematical equivalent in this application means a presentation using essentially the same variables forming the formula.

The liquids to be measured may be e.g. quenching oils used in metal heat treatment processes, refrigerant liquids and heat transfer liquids.

In this application the first $rS_1$ and second measurement step $rS_2$ in connection with formulas 2 and 2a are performed such that absolute water content w stays essentially unchanged between these two measurements. In practice this means with two probes typically a simultaneous measurement with the two probes 30 and 40. Alternatively the measurement may be performed with short intervals with one probe of FIG. 5. The intervals may be some minutes or even hours. In stabile conditions the absolute water content may stay unchanged for long periods, and therefore the method may be performed successfully also with rather long intervals between first $rS_1$ and second measurement step $rS_2$, like intervals of hours or even days.

Monitoring coefficient B essentially continuously means in this application monitoring the coefficient B for weeks, months or even years, in other words long term monitoring, where the above two measurements (the first $rS_1$ and second measurement step $rS_2$) are repeated much more frequently.

The coefficient B could be determined by the first $rS_1$ and second measurement step $rS_2$ e.g., daily or several times in a day and the value of B would be monitored continuously based on these measurements.

LIST OF REFERENCE NUMBERS 10 tank
20 top cooler pipe
30 top temperature probe
30A top temperature sensor
30B top moisture sensor
40 bottom temperature probe
40A bottom temperature sensor
40B bottom moisture sensor
50 bottom cooler pipe
60 windings
70 cooling device
80 transformer
90 oil drying unit
100 cooling bypass pipe
110 first valve
120 second valve
130 input pipe
140 measurement pipe In this application "humidity" or "humidity sensor" means in connection with liquids "relative saturation" or "relative saturation sensor".

The invention claimed is:

1. A method for continuous monitoring of quality and moisture parameters of a liquid, comprising:

a. measuring relative water saturation of the liquid at a first thermodynamic temperature;

b. measuring relative water saturation at a second thermodynamic temperature, provided that absolute water content at the first thermodynamic temperature and absolute water content at the second thermodynamic temperature are essentially equal;

c. determining the absolute water content of the liquid, according to the formula:

$$w = \frac{rS \times \exp\left(A - \frac{B}{T}\right)}{100},$$

or similar mathematical function comprising the same variables, where rS is relative water saturation of the liquid at temperature T;

wherein the water in liquid solubility coefficient A is determined according to the formula $A = \alpha B + \beta$, or similar mathematical function of B, where $\alpha$ and $\beta$ are constants known or experimentally obtained for the liquid, and wherein B is the function of said relative water saturation of the liquid at the first thermodynamic temperature, the relative water saturation of the liquid at the second thermodynamic temperature, and the respective temperatures.

2. The method according to claim 1, wherein the liquid quality is determined by a liquid quality index (LQI) as a function of B water in liquid solubility coefficient, according to the formula $$LQI = 1 - \frac{B_{max} - B}{B_{max} - B_{min}},$$

or similar mathematical function of one or more of the same variables, where Bmax and Bmin are a maximum value and a minimum value of B, respectively, known for the liquid.

3. The method according to claim 1, wherein the Henry's law constant $k_H$ for water in the liquid is determined according to the formula $k_H = \exp(A-B/T)/p_s$ or similar mathematical function of the same variables, where $p_s$ is the saturated water vapour pressure, a function of thermodynamic temperature T.

4. The method in accordance with claim 1, wherein the measurements are performed with two relative saturation sensors along with temperature sensors located in positions of the measurement object such that during measurement there is temperature difference between the sensors.

5. The method in accordance with claim 1, wherein the measurements are performed with two relative saturation sensors along with temperature sensors located in positions of the measurement object such that during measurement the absolute water content (w) remains essentially the same at both locations.

6. A system for continuous monitoring of quality and moisture parameters of a liquid, wherein the system comprises:
   a tank for holding a quantity of a liquid;
   a cooling device;
   a first cooler pipe extending between the tank and the cooling device;
   a second cooler pipe extending between the tank and the cooling device; wherein the second cooler pipe is located a distance away from the first cooler pipe;
   a top moisture and temperature probe provided in the first cooler pipe, wherein the top moisture and temperature probe includes an embedded first temperature sensor and first moisture sensor;
   a bottom moisture and temperature probe provided in the second cooler pipe, wherein the bottom moisture and temperature probe includes an embedded second temperature sensor and second moisture sensor;
   wherein the first moisture sensor is utilized to take a first measurement of a relative water saturation of the liquid at a first thermodynamic temperature;
   wherein the second moisture sensor is utilized to take a second measurement of the relative water saturation at a second thermodynamic temperature;
   performing the first and second measurements such that absolute water content stays essentially unchanged between the first and second measurements; and
   utilizing at least one of the first and second measurements to determining the absolute water content of the liquid.

7. The system, according to claim 6, wherein the above system is also used to determine the liquid quality as a function of solubility coefficient B.

8. The system, according to claim 6, wherein the above system is also used to determine the Henry's Law constant for water dissolution in the liquid.

* * * * *